United States Patent [19]

Chany et al.

[11] 4,041,152

[45] Aug. 9, 1977

[54] PHARMACEUTICAL FORMULATION OF INTERFERON INSOLUBILIZED BY FIXATION ON A SUPPORT

[76] Inventors: Charles Chany, 17, rue Emile-Dubois, Paris, France; Brigitte Galliot, 11, rue Thibaud, Paris, France, 75014; Marie-Josèphe Chevalier, 13, rue Epee de Bois, Paris, France, 75005; Helmut Ankel, 74, av. Denfert-Rochereau, Paris, France, 75674

[21] Appl. No.: 490,658

[22] Filed: July 22, 1974

[30] Foreign Application Priority Data

July 27, 1973 France ................. 73.27538

[51] Int. Cl.² .................... A61K 45/02

[52] U.S. Cl. .................... 424/85
[58] Field of Search .................... 424/85

[56] References Cited

PUBLICATIONS

Wolstenholme et al. – Interferon (1967) pp. 82–84.
Loza et al. – Chem. Abst. vol. 72 (1970) p. 109118 g.
Bourgeade et al. – Chem. Abst. vol. 80 (1971) p. 106,764u.

*Primary Examiner*—Sam Rosen
*Attorney, Agent, or Firm*—Larson, Taylor and Hinds

[57] ABSTRACT

A pharmaceutical product consists of interferon which has been rendered insoluble by being coupled to a support, such as sepharose.

6 Claims, 1 Drawing Figure

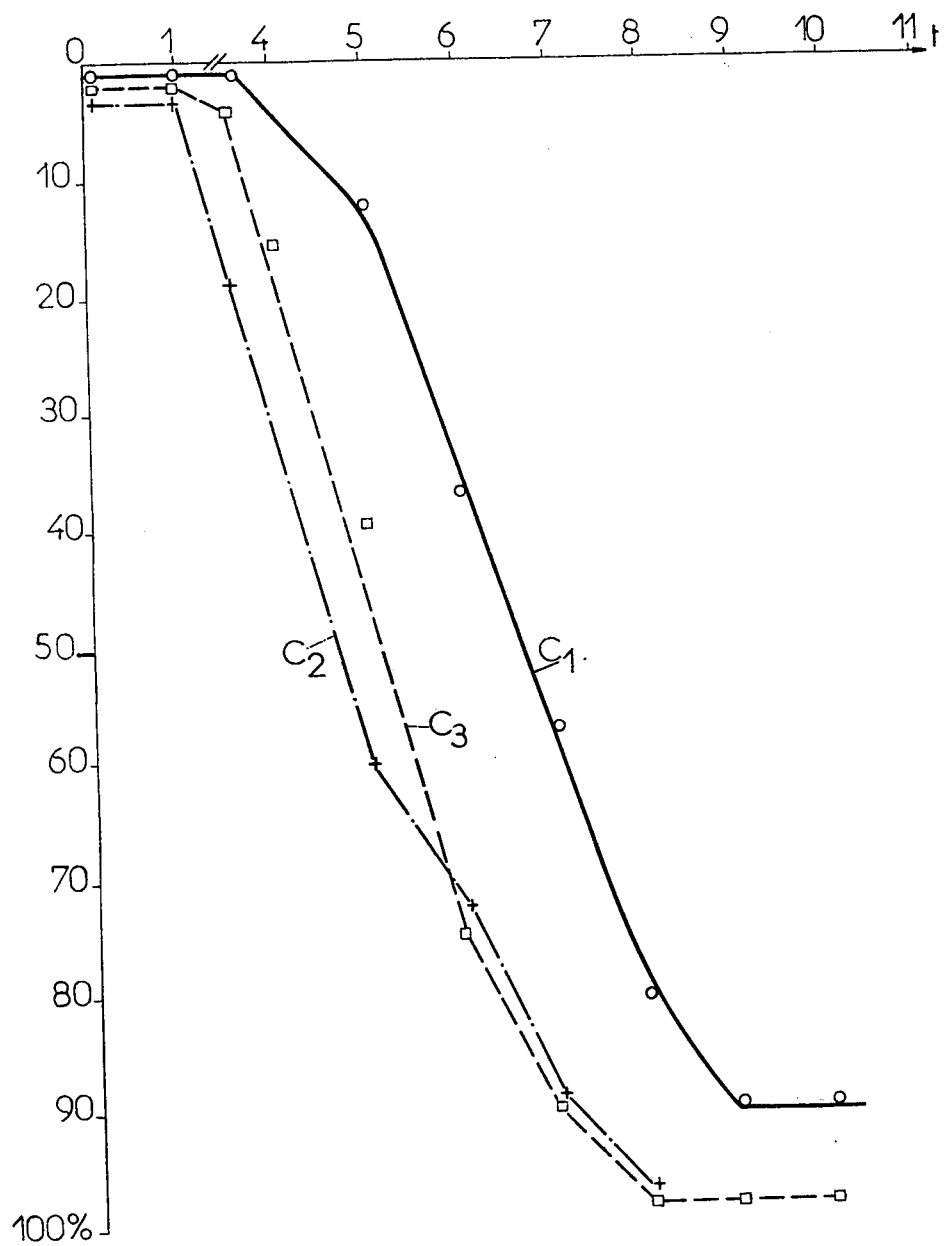

PHARMACEUTICAL FORMULATION OF INTERFERON INSOLUBILIZED BY FIXATION ON A SUPPORT

The subject of the invention is a pharmaceutical form based on interferon, as well as medicines which contain this pharmaceutical form and in which interferon consequently constitutes at least a part of the active substance.

Interferon itself, as well as its therapeutic activity, are well known.

It will be recalled that interferon is a substance of protein nature which is synthesised by the cell and which inhibits the intracellular replication — that is to say the intracellular reproduction — of a wide variety of antigenically distinct viruses, and does so because it blocks all the lytic or carcinogenic manifestations of the said viruses.

It is also known that the practical exploitation of the therapeutic effect of interferon is greatly hindered by the necessity of providing large amounts of interferon - this necessity being due to the fact that this substance is easily destroyed by the cells or proteolytic enzymes and that it must consequently be employed in large amount - which constitutes a serious disadvantage because of the high cost of manufacturing this substance.

The aim of the invention is especially to overcome this disadvantage and to provide a pharmaceutical form and consequently a medicine, which enables the valuable therapeutic properties of interferon to be exploited on a practical basis.

The pharmaceutical form according to the invention consist of interferon which has been rendered insoluble by being coupled to a support.

The medicine according to the invention consists at least partially of the abovementioned pharmaceutical form.

According to a first embodiment, interferon, in the pharmaceutical form according to the invention, is coupled to a support by chemical bonding, and especially by covalent bonds.

According to a second embodiment, interferon, in the pharmaceutical form according to the invention, is coupled to a support by electrostatic forces.

Other characteristics of the invention will become apparent in the course of the description which follows and which relates to various embodiments illustrated by examples.

As has been indicated above, interferon, an example of the preparation of which will be described below, is rendered insoluble by being coupled to a support, and this leads to the pharmaceutical form and consequently to the medicine according to the invention.

The interferon used can be prepared by means of L type cells of mice or "L.M. cells" invaded for 3 hours by the NEWCASTLE disease virus (N.D.V.) and from which the virus has thereafter been removed; a nutrient medium which does not contain any serum, for example some M.E.M. medium ("minimum essential medium" = Eagle medium) is added to these cells; after 24 hours, the supernatural liquid is removed and is kept at pH 2 for 5 days; the medium thus obtained contains interferon.

Further details relating to this preparation will be found in No. 3, volume 132 of the publication "Proc. Soc. Exptl. Biol. and Med., of December 1969.

It will be recalled that the interferon thus obtained is used on other cells of the same type - so-called sensitive cells - each interferon being specific with respect to the type of cells from which it originates.

Thus, in order to treat human patients, an interferon of human origin will be employed. This interferon can, for example, be produced from leucocytes in accordance with the technique described in the article by Ernesto FALCOFF, Rebecca FALCOFF, Francoise FOURNIER and Charles CHANY (Annales de l'Institut Pasteur, volume III, pages 562-584, of November 1966) or from human amniotic membranes, in accordance with the technique of Francoise FOURNIER, Ernesto FALCOFF and Charles CHANY (The Journal of Immunology, volume 99, No. 5, 1967).

According to a first embodiment, the interferon constituting the pharmaceutical form according to the invention, is coupled to a support by chemical bonds and is thus rendered insoluble.

In practice, these chemical bonds are especially covalent bonds, the support being advantageously that known under the tradename "SEPHAROSE", which consists of an agarose gel.

The coupling of interferon to SEPHAROSE by means of covalent bonds necessitates prior activation of the SEPHAROSE.

This activation can be effected by means of cyanogen bromide, the interferon being coupled advantageously by employing the Porath method which will be described below with reference to a numerical example.

Some type 4B SEPHAROSE - in the form of beads of size approximately 0.1 mm — activated by CNBr, is suspended at a concentration of 5 g per 500 ml of $10^{-3}$ M HCl. After swelling, the beads are washed with the same solution of HCl and are then washed twice with 300 ml of a 0.1 M sodium bicarbonate buffer which has been adjusted to pH 8 and contains 0.5 M of NaCl (hereafter called Buffer A).

17 ml of compressed SEPHAROSE gel are thus obtained and are suspended in 30 ml of the abovementioned solution of interferon (prepared in accordance with the method for which the reference was given above, and dialysed for 18 hours at 4° C, against buffer A) containing $10^5$ reference units per ml (Institute of Health).

The suspension of interferon + beads is stirred gently at ambient temperature for 2 hours. After centrifuging, the supernatant liquid is collected and the residue of SEPHAROSE beads is washed with 50 ml of buffer A. The beads are incubated with 50 ml of 1 M ethanolamine at pH 8, for 90 minutes, at ambient temperature, whilst stirring gently, and then they are washed in the following way:

twice with 80 ml of buffer A,
twice with 80 ml of 0.1 sodium acetate buffer containing 1 M of NaCl, at pH 4 (buffer B),
twice with 80 ml of M.E.M. medium,
once with 250 ml of 0.1 sodium borate buffer containing 1 M of NaCl, at pH 8 (buffer C), and
once again with 250 ml of buffer B, again with 250 ml of buffer C and finally three times with M.E.M. medium using 250 ml each time.

The final preparation of Sepharose is suspended in an equal volume of M.E.M. medium.

The SEPHAROSE beads have coupled approximately 90% of the interferon present in the abovementioned solution.

The control preparations of inactivated Sepharose are obtained from SEPHAROSE treated with CNBr and incubated with ethanolamine and then with interferon, the procedure employed being exactly the same as that described above, the only difference being that the incubation with interferon and ethanolamine are reversed. The concentration of proteins in the supernatant liquid, after incubation with the solution of interferon, is 5 mg/ml and $10^5$ interferon units/ml, which shows that no detectable coupling of proteins or of interferon to the SEPHAROSE has taken place.

Instead of using SEPHAROSE beads, it is possible to couple interferon - employing the same techniques as those which have just been described - to dextran, the molecular weight of which is equal to 150,000–200,000 and which is activated beforehand by means of CNBr, the proportions of interferon to support being the same as above.

In a particular experiment, purified interferon, obtained from mice, was coupled to dextran (molecular weight: 60,000), employing the Porath process. Coupled interferon was purified by chromatography on SEPHADEX G 100 and concentrated by pressure dialysis. Each ml contained 3,200–6,400 antiviral units of interferon. The preparation thus obtained will be referred to later.

Other supports which can be suitable within the scope of this same technique are the following polysaccharides:

Homopolysaccharides
Polymers of D-glyclose
   Example: dextran
   Main linkage: $\alpha$-1,6-D-glucosyl-D-glucose
Polymers of D-fructose
   Example: levan
   Main linkage: $\beta$-2,6-D-fructosyl-D-fructose
Polymers of D-mannose
   Example: yeast mannan
   Main linkages: $\alpha$-1,2-, $\alpha$-1,3- and $\alpha$-1,6-D-mannosyl-D-mannose
Polymers of D-galacturonate
   Example: pectin
   Main linkage: $\alpha$-1,4-D-galacturonosyl-D-galacturonate
Polymers of pentoses
   Example: xylan
   Main linkage: $\alpha$-1,4-D-xylosyl-D-xylose
Polymers of D-galactose
   Example: galactan
   Main linkage: $\alpha$-1,4-D-galactosyl-D-galactose
Heteropolysaccharides
Containing modified sugars
   Example: agarose
   Main linkage: $\alpha$-1,4-D-galactosyl-L-3,6-anhydrogalactose
Containing substituted sugars
   Example: glycerol-pectate
   Main linkage: see pectin above
Containing more than one type of monosaccharide residue
   Example: heparin
   Main linkage: $\alpha$-1,4-D-2-deoxy-2-sulphoaminoglucosyl-6-sulphate-D-glucuronate The pharmaceutical form thus obtained constitutes a medicine which is particularly suitable for parenteral administration.

According to a second embodiment, the interferon constituting the pharmaceutical form according to the invention is coupled to a support by electrostatic bonds.

In practice, the support can then consist of, for example, of concavalline A which is a powdery substance extracted from kidney beans.

In order to effect the coupling, a suspension of concavalline A in M.E.M. medium can be mixed with the same solution of interferon as that which was descried above, contact being maintained for a sufficient period of time to couple the maximum amount of interferon; in general, a period of the order of 2 to 6 hours is suitable.

The coupling via electrostatic bonds is not so strong as the coupling via covalent bonds; this can be an advantage if the activity of the interferon in the organism has to be restricted duration; in fact, the relative weakness of the coupling does not prevent gradual liberation of the interferon which is thus destroyed slowly at the instant when it is liberated in the organism.

The pharmaceutical form thus obtained, and especially that in which interferon is coupled to its support by chemical bonds, is noteworthy especially:

in that it can be employed several times in succession, the activity of the interferon being retained, in that interferon coupled in this way is very resistant to the effects of heat in an acid medium, in that interferon coupled in this way acts without apparently penetrating into the cells, and in that even if the interferon is inactivated by the specific anti-interferon serum - its antiviral effect being then inhibited - it can be reactivated if the antigen-antibody complex is broken by treating the pharmaceutical form with a buffer of acid pH.

Because the activity of the pharmaceutical form remains bonded to the support, it is possible to employ relatively small amounts of the pharmaceutical form relative to the number of cells to be treated since, as a result of relative movement, one particle of the pharmaceutical form can be brought into contact in succession with a large number of cells.

The therapeutic effect of coupled interferon can be demonstrated from the information derived from the in vitro experiment which will now be described.

Sensitive L mice cells are treated with the pharmaceutical form, the preparation of which has been described above, and which consists of interferon coupled to SEPHAROSE beads.

Within the scope of this experiment, the said cells are treated with interferon-SEPHAROSE at the rate of 1 bead (diameter No. 0.1 mm) per 4 cells by maintaining contact for 18 hours.

It is possible to go up to a ratio of 25 beads per 1,000 cells.

This contact can be effected by covering a monocellular layer of L cells with a layer of beads, in a Petri dish.

After 18 hours, the SEPHAROSE beads are removed by simply washing with M.E.M liquid, because contact between the beads and the cells is very loose (the beads roll over the surface of the monocellular layer). The cells are then infected with a revealing virus, for example vesicular stomatitis virus (VSV) or encephalomyocarditis virus (EMC) and the yield, after the first replication cycle, is measured using the plate technique.

The protection obtained under these conditions is completely comparable with that achieved in a control experiment using soluble interferon.

This experiment can be repeated at least 4 times without the activity of the pharmaceutical form according to the invention showing a substantial decrease. This possibility is illustrated by the results given in Table I.

TABLE I

Antiviral activity of interferon coupled to SEPHAROSE, before and after 4 cell-to-cell transfers. described

|  | EMC liquid PFU/0.5 ml | VSV PFU/0.5 ml |
|---|---|---|
| Interferon + Sepharose, 4° C | $1.5 \times 10^7$ | $7.4 \times 10^3$ |
| Interferon + Sepharose, 37° C | $3.7 \times 10^7$ | $1.2 \times 10^4$ |
| Interferon + Sepharose after the 4th transfer | $4 \times 10^7$ | $2 \times 10^4$ |
| Control ("Control Virus") | $5.6 \times 10^8$ | $1.2 \times 10^7$ |

PFU = plate-forming units

PFU = plate-forming units

As already emphasised, the interferon constituting the pharmaceutical form according to the invention acts without apparently penetrating into the treated cells.

This characteristic has been demonstrated by means of a group of experiments carried out in the following way.

A monocellular layer of sensitive cells which are to treated was deposited in a first Petri dish, and a central portion of this layer was isolated, for example by means of a ring laid on the monocellular layer.

The surface of the monocellular layer lying inside the ring and consequently isolated from the rest of the layer was brought into contact with a support in the form of SEPHAROSE beads to which interferon was coupled, for example the support of which the preparation is described above.

After the beads had been left in place for 24 hours they are removed and the entire monoceullar layer covering the surface of the Petri dish is inoculated with a virus, for example VSV virus, and then the whole is fixed by means of a layer of agar.

After 48 hours, the attack of the virus is demonstrated by the appearance of plates, all localised outside the central circle, the interior of which corresponds to the surface which was brought into contact with the beads carrying interferon.

In a second experiment, soluble interferon was brought into contact with the surface lying inside the ring; this interferon diffuses throughout the entire monocellular layer, even throughout the part of the surface outside the ring and when the virus referred to above is applied to this layer, the appearance of plates showing the attack of the virus was not observed at all; this can be explained by the fact that soluble interferon has migrated and has come into contact with all the cells.

In a final experiment, SEPHAROSE beads without any interferon were brought into contact with the part of the surface of the monocellular layer lying inside the ring; it is then found that plates due to the attack of the virus appear everywhere, after inoculation.

The stability to heat of the interferon constituting the abovementioned pharmaceutical form has been illustrated by two experiments.

First of all, the pharmaceutical form consisting of interferon coupled to SEPHAROSE beads was heated at 56° C for 1 hour; the insoluble interferon retains all its biological activity whilst, under the same conditions, soluble interferon is almost completely destroyed.

This experiment has been summarised in Table II below:

TABLE II

|  | Haemagglutination EMC* | Yield of the EMC virus in PFU** |
|---|---|---|
| Interferon + Sepharose, 4° C | 64 | $2 \times 10^7$ |
| Interferon + Sepharose, 56° C | 128 | $4.6 \times 10^7$ |
| Soluble inteferon | 256 | $6 \times 10^7$ |
| Soluble interferon, 56° C | 2,048 | $4.6 \times 10^8$ |
| Control virus | 4,096 | $7.4 \times 10^8$ |

*Haemagglutination EMC = haemagglutinating activity of the EMC virus expressed as the inverse of the dilution
**Yield of the EMC virus in PFU = yield with respect to the EMC virus of the infected cell in a single cycle, expressed in "plate-forming units".

In a second experiment, interferon on SEPHAROSE is heated inside an autoclave to a temperature of 110° C under 1 bar, the pH of the solution (in buffer) containing the SEPHAROSE beads to which interferon is coupled, being 2.5 to 7.4.

The experiment lasts for 30 minutes, and at its conclusion it is found that when the pH is 4.6 or less, the antiviral activity of the interferon is practically entirely retained whilst the activity is reduced at pH 7.2.

Table III shows the result of the experiments carried out in an autoclave on L cells.

TABLE III

|  | 30 minutes in an autoclave pH 2.6 | pH 4.6 | pH 7.2 | 30 minutes at 4° C Control- pH 2.6 |
|---|---|---|---|---|
| EMC virus + L cells — Yield | $2 \times 10^4$ | $2 \times 10^4$ | $5.2 \times 10^6$ | $3.6 \times 10^3$ |

Control cell: 0
Control virus: $2.4 \times 10^7$

In the case where soluble interferon in solution at pH 7 is heated in the autoclave, no activity remains.

The value of being able to heat interferon in an autoclave under the abovementioned temperature and pressure conditions resides in the possibility of sterilising the pharmaceutical form in this way.

The ability of the interferon forming the abovementioned pharmaceutical form to recover its therapeutic activity by means of a treatment at an acid pH (of the order of pH 2) after having been inhibited by means of specific anti-interferon serum, is apparent from examining the experiments, the results of which are given in Table IV.

TABLE IV

|  | Haemagglutination EMC | Yield of the EMC virus in PFU |
|---|---|---|
| Interferon + Sepharose | 2 | $4.9 \times 10^5$ |
| Interferon + Sepharose + anti-serum | 2,048 | $2.2 \times 10^8$ |
| Interferon + Sepharose + anti-serum, but treated at pH 2 | 4 | $2.1 \times 10^6$ |
| Control virus | 2,048/4,096 | $2.9 \times 10^8$ |

The value of the pharmaceutical form according to the invention has also been demonstrated by "in vivo" experiments.

A first experiment was carried out on two groups of 20 mice.

100,000 SEPHAROSE beads without any interferon were administered intraperitoneally to the treated animals. Four hours after this administration all the animals (protected animals and control animals) are inoculated with EMC virus. The death rate occurring after this treatment was investigated (see Table V below), and it is seen that interferon coupled to SEPHAROSE provided the treated animals with good protection.

TABLE V

| TIME LAG | Animals which survive after having been treated with interferon + SEPHAROSE and inoculated with EMC virus | Animals which survive after having been treated with SEPHAROSE and inoculated with EMC virus |
|---|---|---|
| 1st day | 20 | 20 |
| 4th day | 19 | 17 |
| 5th day | 16 | 8 |
| 6th day | 10 | 5 |
| 7th day | 5 | 3 |
| 8th day | 4 | 2 |
| 9th day | 3 | 2 |
| 10th day | 3 | 1 |
| 11th day | 2 | 0 |
| 12th day | 1 | 0 |
| 13th day | 1 | 0 |

The fact that, after a relatively long period of time, even the treated animals all finally die can be explained by the fact that, in this experiment, the interferon coupled to beads is localised at a particular site in the animal and cannot escape from this site; now the virus, on the other hand, can circulate and finally attaches itself at other sites of the body where the effect of the interferon can no longer reach it.

A second "in vivo" experiment was carried out using the pharmaceutical form which can be carried by the bloodstream; this form consists of interferon coupled to dextran and has been referred to above. This experiment is illustrated by the single figure which shows the way in which the death rate of the treated animal develops (percentage of animals which die as a function of time, expressed in days).

An amount of 0.2 ml of the abovementioned preparation was inoculated intracerebrally in adult IC mice. Each group consisted of 20 mice. Purified uncoupled interferon was employed as the control, used at a concentration approximately 2–4 times greater. Another control group was injected with tissue culture medium. 200 $LD_{50}$ of virulent encephalomyocarditis virus was then injected at a distant site (intraperitoneally) in each mouse.

As shown in the figure, the 50% survival time of the interferon/dextran-treated animals increased by about 48 hours, whilst uncoupled interferon, although injected at a significantly higher concentration, was ineffective.

This being the case, it is emphasised that the pharmaceutically form according to the invention is of value for many reasons, in the sense that it makes it possible to consider:

conveying interferon through the organism without it being subjected to the effect of inactivating agents;

estracorporeal circulation of blood through containers to the constituent parts of which interferon would be coupled; and the investigation of a wide variety of techniques which would improve the biological effect of interferon.

The fields of application to be considered are all those already known for interferon, that is to say especially all viral diseases and forms of cancers and leukaemias in humans and in animals.

As indicated above, intravenous administration is a particularly advantageous method of administration, the pharmaceutical form used being that in which interferon is coupled to a support such as dextran.

Finally, because of the great stability of the interferon considered within the scope of the pharmaceutical form according to the invention, the latter can play the role of an international standard for interferon.

It is obvious and moreover it is apparent from what has already been stated that the invention is in no way limited to thse methods of these and realisation which have been more especially considered, but, on the contrary, includes all variants thereof.

We claim:

1. A pharmaceutical product comprising an effective amount of interferon rendered insoluble by fixation by way of covalent bonds on a previously activated support selected from the group consisting of agarose, dextran, levan, mannan, pectin, xylan, galactan, glycerol-pectate and heparin.

2. A process for the preparation of the pharmaceutical product according to claim 1 which comprises activating the support by means of the Porath process and then reacting the activated support with the interferon to provide a pharmaceutical product having interferon fixed by covalent bonds to said support.

3. A pharmaceutical composition comprising the product of claim 1 in association with a pharmaceutical carrier.

4. A pharmaceutical product comprising interferon fixed by electrostatic bonds on a support comprising concavallin A.

5. A process for the preparation of the pharmaceutical product according to claim 4 which comprises mixing of a solution of interferon with a suspension of concavallin A in M.E.M. medium, the contact being maintained for a sufficient period of time to couple the maximum amount of interferon.

6. A pharmaceutical composition comprising the product of claim 1 in association with a pharmaceutical carrier.

* * * * *

UNITED STATES PATENT OFFICE
CERTIFICATE OF CORRECTION

PATENT NO. : 4,041,152
DATED : August 9, 1977
INVENTOR(S) : Charles Chaney

It is certified that error appears in the above-identified patent and that said Letters Patent are hereby corrected as shown below:

Claim 1, lines 5-6, change "glycerol-pectate" to

...glyceryl-pectate...

Claim 6, line 2, change "1" to ...4...

Column 3, line 58, change "glycerol-pectate" to

...glyceryl-pectate...

Signed and Sealed this

Twenty-eighth Day of March 1978

[SEAL]

Attest:

RUTH C. MASON
Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,041,152
DATED : August 9, 1977
INVENTOR(S) : Chany et al

It is certified that error appears in the above-identified patent and that said Letters Patent are hereby corrected as shown below:

Change the inventors name "Chaney" to "Chany"

Signed and Sealed this

Sixteenth Day of January 1979

[SEAL]

Attest:

RUTH C. MASON
Attesting Officer

DONALD W. BANNER
Commissioner of Patents and Trademarks